United States Patent [19]

Tajima et al.

[11] Patent Number: 5,116,813
[45] Date of Patent: May 26, 1992

[54] PERFUME COMPOSITION

[75] Inventors: Katsuhiko Tajima; Sachio Tanaka, both of Chiba, Japan

[73] Assignee: Kao Corporation, Tokyo, Japan

[21] Appl. No.: 493,311

[22] Filed: Mar. 14, 1990

[30] Foreign Application Priority Data

Mar. 15, 1989 [JP] Japan .................. 1-62686

[51] Int. Cl.⁵ ............................... A61K 7/46
[52] U.S. Cl. ........................ 512/27; 512/25; 568/448; 568/840
[58] Field of Search ............ 512/25, 27; 568/840, 568/909.5, 448

[56] References Cited

U.S. PATENT DOCUMENTS

| 3,959,396 | 5/1976 | Ochsner et al. | 512/25 |
| 4,476,041 | 10/1984 | Hill et al. | 512/27 |
| 4,758,548 | 7/1988 | Gramlich et al. | 512/25 |

FOREIGN PATENT DOCUMENTS

| 56-108721 | 8/1981 | Japan | 512/25 |
| 56-138109 | 10/1981 | Japan | 512/25 |
| 63-54333 | 3/1988 | Japan | 568/840 |

OTHER PUBLICATIONS

Goodrich et al., Chem. Abst., vol. 90, #36725n (1979).
Sugisawa et al., Chem. Abst., vol. 111, #151,201c (1989).
Srinivas, Chem. Abst., vol. 109, #188,999d (1988).

Primary Examiner—James H. Reamer
Attorney, Agent, or Firm—Birch, Stewart, Kolasch & Birch

[57] ABSTRACT

The present invention relates to a perfume composition comprising a methyl branched aliphatic compound and the methyl branched aliphatic compound useful as perfume material and a method for imparting a fragrance by using such compounds and compositions.

3 Claims, No Drawings

PERFUME COMPOSITION

BACKGROUND OF THE INVENTION

1. Field of the invention.

The present invention is directed to a perfume composition comprising a methyl branched aliphatic compound, a methyl branched aliphatic compound useful as perfume material, and a method for imparting a fragrance by using such compounds and compositions.

2 Description of the Prior Art

Up to the present, many aliphatic aldehydes or aliphatic alcohols are known to be useful as perfume materials. For example, with respect to aliphatic aldehydes having 9-11 carbon atoms, the straight chain aldehydes are known to be useful. With respect to aliphatic aldehydes having one branched methyl group, methylhexylacetoaldehyde (2-methyl octanal), methylheptylacetoaldehyde (2-methyl nonanal), methyloctylacetoaldehyde (2-methyl decanal) and methylnonylacetoaldehyde (2-methylundecanal) are known as perfume materials. Furthermore, some aliphatic aldehydes having one branched methyl group at the $\beta$-position to aldehyde carbon, have been reported only by D. Hagena, K. Bauer et al. [Fragrance and Flavor Substances, 1980, D&PS, Verlag].

On the other hand, with respect to aliphatic alcohols having 9-11 carbon atoms, there are only terpene alcohols such as linalool, geraniol, terpineol, etc., n-nonanol, n-decanol, n-undecanol, which are known as perfume materials.

It is known that the fragrances of perfume compounds are usually quite differentiated by their differences in functional groups or by their small differences in structure.

SUMMARY OF THE INVENTION

Under these circumstances, the present inventors have synthesized many aliphatic alcohols and aldehydes having branched methyl groups and have evaluated their fragrances for the purpose of developing new perfumes and, as a result, found that the aliphatic compound represented by formula (I) and having one methyl group branched at the vicinity at the end of molecule makes the fragrance of various combination perfumes more natural-like when they are used in perfume mixtures. The present invention was accomplished based on the above findings.

Accordingly, the present invention provides for a combination perfume composition which comprises a perfume base; and a fragrance emitting effective amount of the compound having the formula (I)

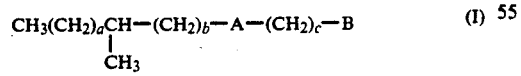  (I)

wherein A represents a —CH$_2$CH$_2$— or a —CH=CH— group, B represents a —CH$_2$OH or a —CHO group, b represents 0 or 1, a+c=3-5 with the proviso that when a+c=3, a is 0 or 1, when a+c=4, a is 0-2 and when a+c=5, a is 0-3.

Among the compounds of the above formula (I), the compound wherein when a+b+c=3, a=0 or 1 and b=0; when a+b+c=4, a=0-2 and b=0; when a+b+c=5, a=1-3 and b=0, or a=0 and b=1, are preferred.

The compound of above formula (I) includes the new compounds represented by the following formula (II), (III), (IV) and (V). Therefore, the present invention also provides for a methyl branched aliphatic compounds represented by the formula (II), (III), (IV) and (V).

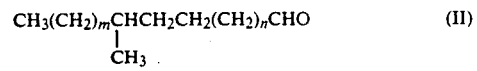  (II)

wherein m and n represent numbers which make m+n=4 or 5, and when m+n=4, m is 2, when m+n=5, m is 0, 2 or 3.

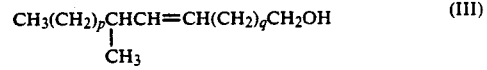  (III)

wherein p and q represent numbers which make p+q=4 or 5, and when p+q=4, p is 1 or 2, when p=q=5, p is 2 or 3.

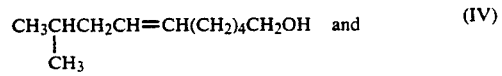  (IV)

and

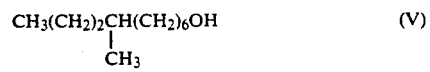  (V)

The present invention is also directed to a method for imparting a fragrance which comprises adding to a perfume base composition a fragrance imparting effective amount of a methyl branched aliphatic compound of the formula (I):

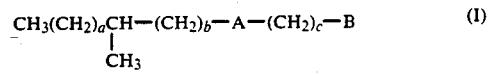  (I)

wherein A represents —CH$_2$CH$_2$— or CH=CH— radical, B represents —CH$_2$OH or —CHO radical, b represents 0 or 1, a+c=3-5 with the proviso that a is o or 1 if a+c=3 a is 0-2 if a+c=4 and a is 0-3 if a+c=5.

DETAILED DESCRIPTION OF THE INVENTION AND PREFERRED EMBODIMENTS

Methyl branched aliphatic compounds (I), which are useful as a material as a component for perfume compositions, can be prepared according to the process by the following reaction formula:

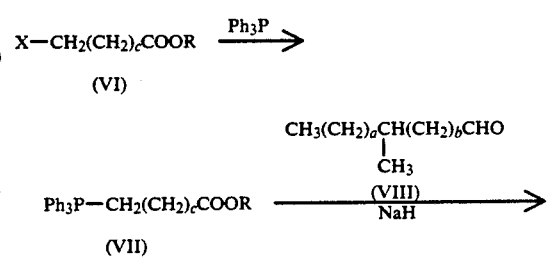

-continued

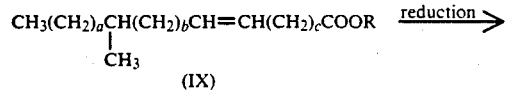
(IX)

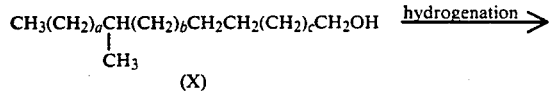
(X)

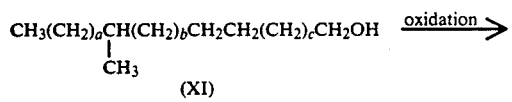
(XI)

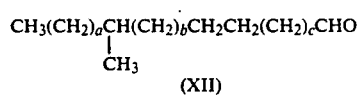
(XII)

wherein X represents a halogen atom, Ph represents a phenyl group, R represents an alkyl group, and a, b and c have the same meaning as defined above.

Namely, methyl branched unsaturated fatty acid esters (IX) can be prepared by reacting fatty acid esters (VI) having a halogen atom at the end of the molecule with triphenyl phosphine to obtain phosphonium salt (VII), and running the Wittig reaction between the resultant product and the α-methyl branched aldehyde (VIII). By reducing the methyl branched unsaturated fatty acid ester (IX), a methyl branched aliphatic unsaturated alcohol, which is included in the methyl branched aliphatic compound of the formula (I), can be prepared. The methyl branched aliphatic alcohol (XI) can then be obtained by hydrogenating compound (X); furthermore, by oxidizing compound (XI), a methyl branched aliphatic aldehyde (XII) can be prepared.

At first, the preparation of a methyl branched unsaturated fatty acid ester (IX) can be practiced under usual Wittig reaction conditions. Namely, compound (VI) can be reacted with triphenyl phosphine in an inert solvent such as acetonitrile, methyl branched aldehyde is then added, and sodium hydride is then carefully added.

The reduction of methyl branched unsaturated fatty acid ester (IX) can be preferably practiced by using a reducing agent such as aluminum lithium hydride, or sodium borohydride.

Hydrogenation of methyl branched aliphatic unsaturated alcohol (X) can be preferably practiced by using palladium carbon, Raney-nickel, Rubidium carbon, Rhodium carbon, etc., as a catalyst.

Oxidation of methyl branched aliphatic alcohol (XI) can be preferably practiced by using an oxidizing agent such as a pyridinium chlorochromate, chromic acid mixture.

The resultant methyl branched aliphatic compounds include new compounds represented by the above formula (II), (III), (IV) and (V). The following are exemplifications of the new compound.

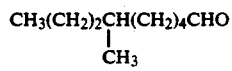

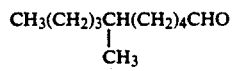

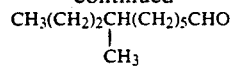

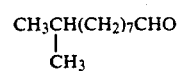

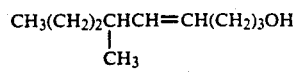

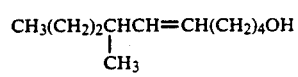

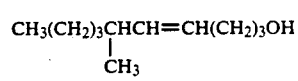

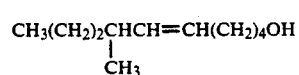

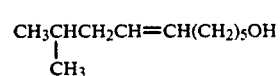

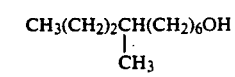

The amount of the methyl branched aliphatic compounds (I) in the perfume composition of the present invention is preferably in the range of 10 ppm to 5 weight %.

Because the methyl branched aliphatic compounds of the formula (I) of the present invention possess citrus or floral odors, as indicated in the test described below, and because their fragrances are extremely strong, they are useful as perfume materials. Accordingly, the perfume compositions of the present invention are applicable in a variety of combination perfumes.

The perfume composition of the present invention can be combined into a variety of base compounds complying with the purpose of the invention.

The present invention is described in detail by way of the following examples and tests.

EXAMPLE 1

Preparation of 8-methyl-6-nonen-1-ol [in formula (I), A=—CH=CH—, B=—CH$_2$OH, a=b=0, c=4]:

223.12 g (1 mol) of ethyl 6-bromohexanoate and 275.4 g (1.05 mol) of triphenyl phosphine were refluxed for 36 hours in 1.5 l of acetonitrile. After the reaction was terminated, 500 ml of acetonitrile was distilled off, then the reaction mixture was dried. Into the dried mixture, 72.11 g (1 mol) of isobutyl aldehyde was added and stirred. Controlling the reaction temperature in the range of 25°–35° C., 40 g (1 mol) of oily (60%) sodium hydride was carefully added. Then, the reaction mixture was stirred over night at room temperature. After the reaction was ended, 500 g of water was added into the reaction mixture, the oil layer was then separated and the water layer was extracted twice with 300 ml of hexane. The organic layers were combined and washed with 300 ml of water, solvent was removed in vacuum under reduced pressure, and then distilled under 2 mm Hg to obtain 122.8 g of ethyl 8-methyl-6-nonenoate (Yield: 62% based upon the starting material).

The product was gradually added dropwise into 1 l of dried ether solution including 11.4 g (0.3 mol) of aluminum lithium hydride under nitrogen atmosphere. The dropwise addition was conducted while the reaction vessel was cooled sufficiently by ice water. After the addition was completed, the reaction temperature was returned to room temperature and stirred for 2 hours. After the reaction ended, 50 g of ethyl acetate was added to the reaction mixture and stirred for 10 minutes. Into the reaction mixture 300 ml of water was added, and the organic layer was separated. The water layer was adjusted to pH 7 and extracted three times with 200 ml of diethyl ether. The organic layers were combined and washed with 200 ml of water, and solvent was removed under reduced pressure to obtain 93.8 g (Yield 97%) of 8-methyl-6-nonen-1-ol.

Boiling Point: 82° C./3mm Hg

IR (liquid film, cm$^{-1}$): 3344, 2932, 1656, 1462, 1378, 1362

$^1$H-NMR (CDCl$_3$ solvent, TMS internal standard, δ): 0.94 (doublet, 6H, J=6.6Hz), 1.25-1 75 (multiplet, 7H), 1.92-2.15 (multiplet, 2H), 2.40-2.70 (multiplet, 1H), 3.63 (triplet, 2H, J=6.2 Hz), 5.04-5.34 (multiplet, 2H)

MS(m/e, relative intensity): 69(100), 57(93), 67(83), 82(78), 81(77), 95(72), 41(65), 56(47), 68(34), 57(33)

EXAMPLE 2

Preparation of 8-methyl nonanol [in formula (I), A=—CH$_2$CH$_2$—, B=—CH$_2$OH, a=b=0, c=4]:

93.8 g of 8-methyl-6-nonen-1-ol, which was prepared in example 1, and 14.1 g of 5% Palladium carbon were agitated for 1 hour in an autoclave at a reaction temperature of 60° C. under 100 kg/cm$^2$ of hydrogen pressure. After the reaction ended, Palladium carbon was filtered off to obtain 91.0 g of 8-methyl nonanol (Yield 95.8%).

Boiling Point: 87° C./2.5 mmHg

IR (liquid film, cm$^{-1}$): 3340, 2927, 1467, 1384, 1367

$^1$H-NMR (CDCl$_3$ solvent, TMS internal standard, δ): 0.85 (doublet, 6H, J=6.2 Hz), 1.15-1.70 (multiplet, 7 H), 3.62 (multiplet, 2H)

MS(m/e, relative intensity): 56(100), 69(76), 55(69), 57(56), 43(36), 84(28), 97(23), 68(14)

EXAMPLE 3

Preparation of 8-methyl nonanal [in formula (I), A=—CH$_2$CH$_2$—, B=—CHO, a=b=0, c=4]:

91.0 g of 8-methyl nonanol, which was prepared in Example 2, was added dropwise into a mixture solution of 1.5 l of dichloromethane and 194 g (0.9 mol) of pyridinium chlorochromate, and the mixture was stirred for 2 hours at room temperature. Into the reaction mixture 3 l of diethyl ether was added, the mixture was passed through 500 g of florisil and solvent was evaporated off. The crude product obtained was distilled to obtain 77.5 g of 8-methyl nonanol (Yield 86.3%).

Boiling point: 66° C./2 mmHg.

IR (liquid film, CM$^{-1}$): 2950, 1730, 1470, 1385, 1375

$^1$H-NMR (CD Cl$_3$ solvent, TMS internal standard, δ): 0.87 (doublet, 6H, J=6.2 Hz), 1.20-1.72 (multiplet, 11H), 2.43 (triplet, 2H, J=7.5 Hz), 9.76 (triplet, 1H, J-1.8 Hz)

MS (m/e, relative intensity): 57(100), 82(65), 43(57), 69(55), 55(52), 56(49), 41(48), 72(42), 81(38), 95(37)

EXAMPLE 4

Preparation of 7-methyl-5-decen-1-ol [in formula (I), A=—CH=CH— B=—CH$_2$OH, a=2, b=0, c=3]:

104.54 g (0.5 mol) of ethyl 5-bromovalerate and 137.5 g (0.525 mol) of triphenyl phosphine were refluxed for 36 hours in 1 l of acetonitrile. After the reaction terminated, 500 ml of acetonitrile was distilled off, then the reaction mixture was dried. Under nitrogen atmosphere, 50.1 g (0.5 mol) of 2-methyl valeraldehyde was added, then the reaction mixture was stirred. Controlling the reaction temperature to within the range of 25°-35° C., 20.0 g (0.5 mol) of oily (60%) sodium hydride was added little by little. After the addition, the reaction mixture was stirred over night at room temperature. After the reaction ended, 250 g of water was added into the reaction mixture, then oil layer was separated and the water layer was extracted three times with 150 ml of hexane. The organic layers were combined and washed with 150 ml of water. After the hexane solution was dried sufficiently with anhydrous Magnesium sulfate, solvent was removed under reduced pressure, and distilled to obtain 57.3 g of ethyl 7-methyl-5-decenoate (Yield: 54%, based upon starting material). The product was gradually added dropwise into 500 ml of dried ethylether solution including 5.12 g (0.135 mol) of aluminum lithium hydride under nitrogen stream. The dropwise addition was done while a reaction vessel was cooled sufficiently by ice water. After the addition was completed, the reaction temperature was returned to room temperature and stirred for 2 hours. Then, 300 ml of water was added gradually into the reaction mixture, and the organic layer was separated. The water layer was returned to pH7 and extracted three times with 100 ml of diethylether. The organic layers were combined and washed with 100 ml of water, and solvent was removed from the reaction mixture under reduced pressure to obtain 44.2g of 7-methyl-5-decen-1-ol (Yield: 52", based upon starting material).

IR (liquid film, cm$^{-1}$): 3345, 2958, 1457, 1066

$^1$H-NMR (CDCl$_3$ solvent, TMS internal standard, δ): 0.88 (triplet, 3H), 0.92 (doublet, 3H, J=6.6 Hz), 1.15-1.35 (multiplet, 4H), 1.40-1.68 (multiplet, 5H), 1.96-2.15 (multiplet, 2H), 2.20-2.58 (multiplet, 1H), 3.36-3.70 (multiplet, 2H), 5.00-5.45 (multiplet, 2H)

MS (m/e, relative intensity): 67(100), 109(93), 55(90), 81(76), 95(42), 68(31), 41(30), 56(22), 82(20), 84(20)

EXAMPLE 5

Preparation of 7-methyl decanol [in formula (I), A=—CH$_2$CH$_2$—, B=—CH$_2$OH, a=2, b=0, c=3]:

44 g (26 mol) of 7-methyl-5-decen-1-ol, Which was prepared in Example 4, and 6.6 g of 5% Palladium carbon were agitated for 1 hour in an autoclave at a reaction temperature of 60° C. under 100 kg/cm$^2$ of hydrogen pressure. After the reaction ended, Palladium carbon was filtered off to obtain 7-methyl decanol.

Amount: 43.5 g (Yield 97%)

Boiling point: 93 C/3 mmHg)

IR (liquid film, cm 3340, 2926, 1463, 1378, 1058

$^1$H-NMR (CDCl$_3$ solvent, TMS internal standard, δ): 0.80-0.95 (multiplet, 6H) 1.18-1.70 (multiplet, 16H) 3.67 (triplet, 2H, J=6.3 Hz)

MS (m/e, relative intensity): 69(100, 55(71), 84(49), 43(48), 70(43), 111(35), 56(33), 41(32), 83(29), 71(23)

EXAMPLE 6

Preparation of 7-methyl decanal [in the formula (I), A=—CH$_2$CH2—, B=—CHO, a=2, b=0, c=3]:

43.5 g (0.25 mol) of 7-methyl decanol, which was prepared in Example 5, was added into a mixture solution of 500 ml of dichloromethane and 81.9 g (0.38 mol)

of pyridinium chlorochromate, and the reaction mixture was stirred for 2 hours at room temperature. Into the reaction mixture 2 l of diethyl ether was added, the mixture was passed through 300 g of florisil, and then solvent was evaporated off. The crude product obtained was distilled to obtain 7-methyl decanal.

Amount: 31.1 g (Yield: 73%):
Boiling point: 83.5° C./4 mmHg)
IR (liquid film, cm$^{-1}$): 2932, 1729, 1466, 1379
$^1$H-NMR (CDCl$_3$ solvent, TMS internal standard, δ): 0.8–0.92 (multiplet, 6H), 1.20–1.80 (multiplet, 13H), 2.43 (triplet, 2H, J=6.6 Hz), 9.76 (triplet, 1H, J=1.8 Hz)
MS (m/e, relative intensity): 109(100), 43(92), 55(88), 57(73), 84(71), 67(67), 41(58), 71(52), 85(50), 83(39)

EXAMPLE 7

Preparation of 6-methyl-4-nonen-1-ol [in formula (I), A=—CH=CH—, B=—CH$_2$OH, a=2, b=0, c=2]:

6-methyl-4-nonen-1-ol was prepared in the same manner according to Example 4 except that 97.5 g (0.5 mol) of ethyl-4-bromobutylate was used in place of ethyl 5-bromovalerate as starting material in Example 4.

Amount: 41.2 g (Yield: 54%, based upon starting material)
IR (liquid film, cm$^{-1}$): 3323, 2957, 1456, 1062
$^1$H-NMR (CDCl$_3$ solvent, TMS internal standard, δ): 0.88 (triplet, 3H, J=6.3 Hz), 0.92 (doublet, 3H, J=6.6 Hz), 1.10–1.35 (multiplet, 4H), 1 54–1.72 (multiplet, 3H), 2.08 (triplet, 2H, J=6.9 Hz), 2.12–2.58 (multiplet, 1H), 3.65 (multiplet, 2H, J=6.4 Hz), 5.15–5.39 (multiplet, 2H)
MS (m/e, relative internal): 95(100), 55(65), 67(54), 41(30), 69(29), 81(23), 96(22), 68(19), 84(17), 43(16)

EXAMPLE 8

Preparation of 6-methyl nonanol [in formula (I), A=—CH$_2$CH$_2$—, B=—CH$_2$OH, a=2, b=0, c=2]:

41.2 g (0.26 mol) of 6-methyl-4-nonen-1-ol, which was prepared in Example 7, was hydrogenated in the same manner according to Example 5 to obtain 2-methyl nonanol (amount: 38.68 g, Yield 94%). The alcohol was oxidized in the same manner according to Example 6 to obtain 6-methyl nonanol.

Amount: 31.3 g (Yield 81%)
Boiling point: 64° C./3 mmHg
IR (liquid film, cm$^{-1}$): 2927, 1729, 1465, 1379
$^1$H-NMR (CDCl$_3$ solvent, TMS internal standard, δ): 0.81–0.96 (multiplet, 6H) 1.16–1.70 (multiplet, 11H) 2.44 (triplet, 2H, J=7.0 Hz) 9.76 (triplet, 1H, J=2.0 Hz)
MS (m/e, relative intensity): 43(100), 95(89), 71(70), 57(69), 70(67), 69 66 , 55(58 , 41(56), 84(36), 96(36)

EXAMPLE 9

Preparation of 7-methyl-5-nonen-1-ol [in formula (I), A=—CH=CH—, B=—CH$_2$OH, a=1, b=0, c=3]

7-methyl-5-nonen-1-ol was prepared in the same manner according to Example 4 except that 43.07 g (0.5 mol) of 2-methyl butylaldehyde was used in place of ethyl 2-methyl valeraldehyde.

Amount: 44.5 g (Yield: 57% based upon starting material)
Boiling point: 90.5° C./3 mmHg
IR (liquid film, cm$^{-1}$): 3345, 2958, 1457, 1066
$^1$H-NMR (CDCl$_3$ solvent TMS internal standard δ): 0.84 (triplet, 3H, J=6.9 Hz), 0.92 (doublet, 3H, J=6.8 Hz), 1.15–1.65 (multiplet, 6H), 1.82 (singlet, 1H), 2.03 (triplet, 2H), 2.10–2.50 (multiplet, 1H), 3.63 (triplet, 2H, J=6.4 Hz), 5.12–5.39 (triplet, 2H)

MS (m/e, relative intensity): 55(100), 109(79), 67(78), 81(61), 70(47), 41(37), 83(31), 69(30), 68(25), 57(24)

EXAMPLE 10

Preparation of 6-methyl-4-decen-1-ol [in formula (I), A=—CH=CH-, B=—CH$_2$OH, a=3, b=0, c=2]

6-methyl-4-decen-1-ol was prepared in the same manner according to Example 4 except that 97.5 g (0.5 mol) of ethyl 4-bromobutyrate was used in place of ethyl 5-bromovalerate and 57.1 g (0.5 mol) of 2-methyl hexanal was used in place of 2-methyl valeraldehyde.

Amount 44.3 g (Yield: 52%, based upon starting material)
Boiling point: 90° C./3 mmHg
IR (liquid film, cm$^{-1}$) 3325, 2957, 1457, 1061
$^1$H-NMR (CDCl$_3$ solvent, TMS internal standard, δ): 0.82–0.96 (multiplet, 6H), 1.16–1.35 (multiplet, 6H), 1.66 (multiplet, 3H), 2.07 (triplet, 2H, J=6.8 Hz), 2.20–2.56 (multiplet, 1H), 3.64 (triplet, 2H, J=6.3 Hz), 5.04–5.40 (multiplet, 2H)
MS (m/e, relative intensity): 95(100), 67(68), 55(62), 69(50), 81(41), 41(33), 82(24), 96(23), 68(23), 56(20)

EXAMPLE 11

Preparation of 6-methyl decanol [in formula (I), A=—CH$_2$CH$_2$, B=—CHO, a=3, b=0, c=2]:

44.3 g (0.26 mol) of 6-methyl-4-decen-1-ol, which was prepared in Example 10, was hydrogenated according to Example 5 to obtain 6-methyl decanol (amount 37.1 g, yield 90%). The alcohol was oxidized according to Example 6 to obtain 6-methyl decanal.

Amount: 37.1 g (Yield: 90%)
Boiling point: 76.5° C./3 mmHg)
IR (liquid film, cm$^{-1}$): 2929, 1729, 1463, 1378
$^1$H-NMR (CDCl$_3$ solvent, TMS internal standard, δ): 0.84–0.96 (multiplet, 6H), 1.20–1.76 (multiplet, 13H), 2.43 (triplet, 2H, J=7.0 Hz), 9.76 (triplet, 1H, J=1.8 Hz)
MS (m/e, relative intensity): 43(100), 95(85), 57(81), 69(76), 85(59), 41(58), 84(53), 55(46), 96(39), 67(32)

EXAMPLE 12

Preparation of 9-methyl-6-decen-1-ol [in formula (I), A=—CH=CH—, B=—CH$_2$OH, a=0, b=1, c=4]:

9-methyl-6-decen-1-ol was prepared in the same manner according to Example 4 except that 111.56 g (0.5 mol) of ethyl 6-bromohexanoate was used in place of ethyl 5-bromovalerate and 43.07 g (0.5 mol) of isovaleraldehyde was used in place of 2-methyl valeraldehyde.

Amount: 42.6 g (Yield: 50%, based upon starting material)
IR (liquid film, cm$^{-1}$): 3336, 2932, 1465, 1383, 1363, 1055
$^1$H-NMR (CDCl$_3$ solvent, TMS internal standard, δ): 0.89 (doublet, 6H, J=6.2 Hz), 1.24–1.64 (multiplet, 9H), 3.62 (triplet, 2H), 5.32–5.45 (multiplet, 2H),
MS (m/e, relative intensity): 67(100), 55(65), 81(56), 95(48), 82(46), 69(41), 68(38), 41(37), 56(33), 43(30)

EXAMPLE 13

Preparation of 9-methyl decanol [in formula (I), A=—CH$_2$CH$_3$—, B=—CH$_2$OH, a=0, b=1, c=4]and 9-methyl decanal [in formula (I), A=—CH$_2$CH$_2$—, B=—CH0, a=0, b=1, c=4]:

42 6 g (0.25 mol) of 9-methyl-7-decen-1-ol, which was prepared in Example 12, was hydrogenated according to Example 5 to obtain 9-methyl decanol (amount: 41.8 g, yield: 97%). The alcohol was oxidized according to Example 6 to obtain 9-methyl decanal.

Amount: 34.3 g (Yield: 83%)
Boiling point: 77° C./3 mmHg
IR (liquid film, cm$^{-1}$): 2927, 1730, 1467, 1386, 1367
$^1$H-NMR (CDCl$_3$ solvent, TMS internal standard, δ): 0.86 (doublet, 6H, J=6.2 Hz), 1.20-1.70 (multiplet, 13H), 2.43 (triplet, 1H, J=6.4 Hz), 9.76 (triplet, 1H, J=2.0 Hz)
MS (m/e, relative intensity): 57(100), 43(74), 69(69)

Test 1

The fragrances of the methyl branched aliphatic compounds (I), which are combined into the perfume composition of the present invention, were examined. The results are shown in Table 1.

TABLE 1

| Compound of the formula (I) | odor description |
|---|---|
| 6-methyl octanal | fruity, green, sweet aldehyde |
| 7-methyl octanal | lemon, sweet, green, woody lactone |
| 6-methyl nonanal | green, iris, waxy |
| 7-methyl nonanal | citrus, muguet, waxy |
| 8-methyl nonanal | citrus, sweet, waxy, milky |
| 6-methyl decanal | green, aldehyde |
| 7-methyl decanal | citris, green, aldehyde, fatty |
| 8-methyl decanal | sweet, rosy, adelhyde |
| 9-methyl decanal | green, fatty, aldehyde |
| 6-methyl-4-octen-1-ol | green, violet, spicy |
| 7-methyl-5-octen-1-ol | green, geranium, floral, fatty |
| 6-methyl-4-nonen-1-ol | citrus, green, fresh |
| 7-methyl-5-nonen-1-ol | green, citrus |
| 8-methyl-6-nonen-1-ol | citrus, rosy, sweet, melon |
| 6-methyl-4-decen-1-ol | citrus, floral, green, waxy |
| 7-methyl-5-decen-1-ol | stale smell |
| 8-methyl-6-decen-1-ol | rosy, powdery, floral |
| 9-methyl-7-decen-1-ol | green, aldehyde, balsam |
| 6-methyl octanol | green, rosy, floral, citrus, fresh, iris |
| 7-methyl octanol | green, citrus, floral, fatty |
| 6-methyl nonanol | green, iris, citrus, floral |
| 7-methyl nonanol | rosy, powdery, fatty |
| 8-methyl nonanol | green, fatty, floral, rosy |
| 6-methyl decanol | green, fatty |
| 7-methyl decanol | green, sweet, floral |
| 8-methyl decanol | floral, rosy, green |
| 9-methyl decanol | fatty, oily |

From Table 1, the fragrance of the aldehydes having a branched methyl group according to the present invention has, in comparison with the aldehydes without a branched methyl group, a characteristic smell which is reduced with respect to the particular aldehyde odor and enhanced with respect to the particular citrus and floral odors. The fragrances of the methyl branched alcohols also have strong floral, fruity and green leafy odors, unlike the usual alcohols.

Test 2

In order to evaluate the strength of the fragrance, the odor threshold of the fragrance was measured by ten professional panelists.

Test Method

The odor threshold was evaluated by using the triangle comparison method as set forth in Larmond, E., ASTM Spec. Tech. Publ. 1974, 594.

Test Result

The result regarding 8-methyl nonanal is described below. 2-methyl decanal and n-undecanol were used as comparative samples. Though the odor threshold of 2-methyl decanal and n-undecanal were both 5.0 ppm, the odor threshold of 8-methyl nonanal of the present invention was 0.01 ppm.

EXAMPLE 14

Preparation of a perfume composition containing 8-methyl-6-nonen-1-ol

| ROSE BASE: | (parts by weight) |
|---|---|
| geranium bourbon | 10 |
| citronellol | 100 |
| geraniol | 50 |
| nerol | 30 |
| phenylethyl alcohol | 600 |
| diphenyl oxide | 5 |
| linalool | 15 |
| geranyl acetate | 10 |
| eugenol | 10 |
| decenol | 1 |
| phenylacetic acid 9.9% (phenylethyl alcohol) | 10 |
| methyl phenylacetate | 20 |
| bees wax absolute | 5 |
| dipropylene glycol | 124 |
| TOTAL | 990 |

Into 990 parts by total weight of rose base described above, 10 parts by weight of 8-methyl-6-nonen-1-ol was added, and ten professional panelists evaluated the added composition of the present invention and non-added comparative composition. All ten panelists found that the composition of the present invention has a stronger and enhanced natural floral rose base odor.

EXAMPLE 15

Preparation of a perfume composition containing 8-methylnonanal

| MANDARIN BASE: | parts by weight |
|---|---|
| α-pinene | 20 |
| β-pinene | 10 |
| myrcene | 10 |
| limonene | 484 |
| lemon terpene | 100 |
| orange valencia | 200 |
| γ-terpinene | 150 |
| mandarin aldehyde 10(%)* | 10 |
| thyme red | 5 |
| dimethyl anthranilate | 5 |
| coumarin | 1 |
| carrot seed oil | 1 |
| geranyl methyl carbinyl acetate | 2 |
| TOTAL | 998 |

*produced by Firmenich SA specialty chemical cis -3-dodecenal

Into 998 parts by total weight of Mandarin base described above, w parts by weight of 8-methyl nonanal was added, and ten professional panelists evaluated the added composition (the present invention) and non-added comparative composition. Nine panelists found that the composition of the present invention has much peel-like feeling and enhanced natural citrus odors.

Methyl branched aliphatic compounds (I) of the present invention have citrus, floral, green or fruity fragrances, and the fragrances are extremely strong. Therefore, the perfume composition of the present invention comprising a methyl branched aliphatic compound (I) can emit, for example, much peel-like odor to reach a more natural citrus-like perfume composition, and emit a sweet odor to reach a more natural floral-like perfume composition; and furthermore, emit a more transparent feeling as to a fruity perfume composition. Accordingly, the perfume composition of the present invention is superior as a material for a variety of combinations, and widely applicable to combination perfumes for dishwasher detergents, heavy duty detergents, softeners, fragrant agents, shampoos, rinses, cosmetics, soaps, etc.

Having thus described the invention, it is to be noted that the same can be modified without departing from the spirit and scope of the invention.

What is claimed:

1. A combination perfume composition which comprises a perfume base; and
   a fragrance emitting effective amount of a compound selected from the group consisting of 8-methyl nonanal, 8-methyl decanal, 9-methyl decanal, 8-methyl nonanol, 8-methyl decanol, and 9-methyl decanol.

2. The composition according to claim 1 wherein the amount of said compound is in the range of 10 ppm to 5 wt % based on the total weight of the combination perfume.

3. A method for imparting a fragrance to a perfume base composition which comprises adding to said perfume base composition a fragrance imparting effective amount of a methyl branched aliphatic compound selected from the group consisting of 8-methyl nonanal, 8-methyl decanal, 9-methyl decanal, 8-methyl nonanol, 8-methyl decanol, and 9-methyl decanol.

* * * * *